United States Patent Office

Plant Pat. 1,370
Patented Mar. 29, 1955

1,370

ROSE PLANT

Josephine D. Brownell, Little Compton, R. I.

No Drawing. Application December 14, 1953, Serial No. 398,239

1 Claim. (Cl. 47—61)

My invention relates to roses and especially to a new, original and distinct variety of the class known commercially as hardy large flowered climber and is a variant in that class, being a *Rosa wichuraiana* hybrid tea hybrid, in combination with cane growth usually common to climbing roses only, except that the canes of my new rose usually bear blooms normally as once bloom climbers and my new rose also produces normal hybrid tea type of growth that blooms in the normal hybrid tea manner, especially as to recurrent bloom; discovered in part for me and under my direction in the propagating grounds for me in the town of Milford, Delaware.

My new rose is new, in that it is a climbing sport of the Sub Zero *Rosa wichuraiana* hybrid tea variety "Red Duchess," Plant Patent No. 846. Because of this variation it has acquired the characteristic of intense rebloom growth and bloom at the terminal end of the cane growth, the year such canes grow, at maturity of the cane and retained the hybrid tea type of growth.

My new rose has been asexually reproduced by skin grafting (commonly called budding) on or about July 12, 1951, and disclosed the same characteristics as the parent plant from which the budded eye was taken. This was done at my hybridizing fields in Little Compton, Rhode Island.

Other than the changes specified above my new rose is the same as "Red Duchess."

No drawing is submitted because the only difference from "Red Duchess" is the addition of normal intense rebloom growth.

I claim:

A new and distinct variety of hardy *Rosa wichuraiana* hybrid plant substantially as herein described characterized by the features of its parent variety "Red Duchess" with the additional features of climbing habit, and retaining the feaures of hybrid teas and rebloom.

No references cited.